United States Patent [19]
Guilloux et al.

[11] Patent Number: 5,821,122
[45] Date of Patent: Oct. 13, 1998

[54] ISOLATED NUCLEIC ACID MOLECULES, PEPTIDES WHICH FORM COMPLEXES WITH MHC MOLECULE HLA-A2 AND USES THEREOF

[75] Inventors: Yannick Guilloux; Francine Jotereau, both of Nantes, France; Thierry Boon-Falleur, Brussels, Belgium; Sophie Lucas, Brussels, Belgium; Vincent Brichard, Brussels, Belgium

[73] Assignee: Inserm (Institute Nat'l de la Sante et de la Recherche . .), Paris, France

[21] Appl. No.: 487,135

[22] Filed: Jun. 7, 1995

[51] Int. Cl.[6] .................................................. C07H 21/00
[52] U.S. Cl. ........................ 435/325; 435/252.3; 536/23.1
[58] Field of Search .............................. 435/240.2, 320.1, 435/252.3, 254.11, 240.4, 254.2, 325; 536/23.1

[56] References Cited

U.S. PATENT DOCUMENTS 5,342,774   8/1994   Boom et al. ......................... 435/240.2

OTHER PUBLICATIONS

Saito, H. et al. (1994) cDNA Cloning and Chromosomal Mapping of Human N-acetylglucosaminyltransferase V. Biochem. Res. Comm. 198 (1) pp. 318–327, 1994.
Coulie et al., *J. Exp. Med.,* 18:35–42 (1994).
Saito et al., *Biochem. Biophys. Res. Commun.,* 198:318 (1994).
Viret et al., *Eur. J. Immunol.,* 23:141–146 (1993).
Barinaga *Science,* 257: 880 (1992).
Fremont et al., *Science,* 257: 919 (1992).
Latron et al., *Science,* 257: 964 (1992).
Traversari et al., *Immunogenetics,* 35:145 (1992).
Pandolfino et al., *Eur. J. Immunol.,* 22:1795–1802 (1992).
Reddel et al., *Science,* 257:238 (1992).
van der Bruggen et al., *Science,* 254:1643 (1991).
Lynch et al., *Eur. J. Immunol.,* 21:1403–1410 (1991).
Chen et al., *Proc. Natl. Acad. Sci. USA,* 88:110–114 (1991).
Van den Eynde et al., *Int. J. Cancer,* 44:634–640 (1989).
Kast et al., *Cell,* 59:603–614 (1989).
Boon et al., *J. Exp. Med.,* 152:1184–1193 (1988).
Frohman et al., *Proc. Natl. Acad. Sci. USA,* 851:8998–9002 (1988).
Male et al., *Advanced Immunology* (J.P. Lipincott Company) (1987).
Hérin, et al., *Int. J. Cancer,* 39:390–396 (1987).
Davis et al., *Basic Methods in Molecular Biology,* Elsevier, New York, pp. 130–135 (1986).
Greenberg, *J. Immunol.,* 136(5):1917 (1986).
Maniatis et al., in *Molecular Cloning: A Laboratory Manual* (Cold Spring Harbor, N.Y.) (1982).

*Primary Examiner*—Robert A. Wax
*Assistant Examiner*—Enrique D. Longton
*Attorney, Agent, or Firm*—Felfe & Lynch

[57] ABSTRACT

New tumor rejection antigen precursors, and the nucleic acid molecules which code for them, are disclosed. These tumor rejection antigen precursors are referred to as NAG tumor rejection antigen precursors, and the nucleic acid molecules which code for them are referred to as NAG coding molecules. Various diagnostic and therapeutic uses of the coding sequences and the tumor rejection antigen precursor molecules are described.

16 Claims, 7 Drawing Sheets

FIG. 6

5' extremity of 14 kb insert containing exon +1526 to +1675 of GnT V cDNA (in bold).

agaagttctagtccagatacaggttgttatgcaaatgaaagagaaagttcttgtgcttgttttattattagAAT
AAGAAGATCTACTTGGACACATTATTCACACATACATGGAAGTGCATGCAACTGTTATGGCTCCAGCACAAAGAATATTCC
CAGTTACGTGAAAAACCATGGTATCCTCAGTGGACGGGACCTGCAGTTCCTTCTTCGAGAAACCAAGgtaaaattcacc
acggatgtgttcaggttattgccattggctatgaaaatggatcagaatatttcatgcttgttttcaagtgctgcaat
aaactcttgtgctattt 3' extremity of 14 kb insert containing exon +1676 to +1822 of GnT V cDNA (in bold).

attgctgtgaaaagaccgaggaaaacagaaccaagcttgcagctaaatctagttgagccatctcctcattctcaaca
cctggccttgtggttgggtgatgctctgtgatggcagaaggtaaggacgccctgggccagttatctttctcacttaa
tgtgcccctgggggctgaaacagaacaggcttttatgtggtagagaaggacacagcttcgtcaagccagacctgaccc
tgcccatcaaccactgcctccagcagtgctccaggaaatcagcaccactgaactgcagcttgtcccttgtcgtgagc
agttattcattttggaccagcaagttgttgctgccatctatggtctgcgtctctatggtcccccctgtctgttcccagctgc
tgtggttgctctgaggactgagagcagttgcccttgcagcttcagcaagctgttgagagcacatggttgcctgct
ggagagggaagcagctgccccagtgtaaacccattatgaaaactgtgtttactgaccatcattttaaagcagttccgtttgaac
ttggtgtcccagtgctaaacctccaagtgaccttctgtcctccgcagcattcctgaaagggctgttgttcttttgttcaatga
agaaaccttctgtgtagttaagcaagtgtttttctttaatactccatctcccgtggttagtgagttacagaaggattatgttgggtctt
ggtggtggtggttgttgttttctttcttaataactccatctcccgtgatacccgtagtcgtagacacttaattttttagtt
ccttggtggaggagagcatagtgagttgagcagttgagcagtttgtggacttaaaagttcgtagttttcagatcctggtgtaag
ctgaattctctctgccccaccccaggcgtgggagccttccaaagtgaggtgtccacggaatgaggtgccacagaatc VLPDVFIRC    nonapeptide
gccgcctgcaagctaggaatgccgtcctgcctgATGgtcctgcctgatgtgttcatacgctg|gtggttttctgtctta
cagTTGTTTGTTGGACTTGGGTTCCCTTACGAGGCCCAGCTCCCCTGGAAGCTATCGCAAATGGATGTGCTTTTCTGAA
TCCCAAGTTCAACCCACCCAAAAGCAGCAGCAAAACACAGCCTTTTTCATTGGTGAGCCAACTCTGAGAGAGgtaagcatct
atcaaattattccatttgaataatatgaatagctcatgtgctcatgtagtattaaccttccatctaa
catgattggggaggggtgaggtatagagagctcagagagcaaatgacctgatcctcgagctc 1 → PCR A-B for GnT.V messenger    2 ←

3 → PCR 1-C for NA17-A messenger    4 ←

FIG. 9

COMPLETE NA17-A cDNA (compilation of 3' and 5' RACE results).

atcctcctacccgtgatacccctagacactaattttttagttcctggtggagagagcatagtgagttgagcagctt
tgtgggactttaaaagttcgtagttttcagatcctggtgtaagctgaattctctgccccaccccaggcctggga
gccttccaaagtgaggtgtccacagagtgccacagaatcgccgcctgcacagaatgccgtcctgcctgat
ggtcctgcctgatgtgttcatacgctgtgtggttttctgtcttacag**TTGTTTGTTGGACTTGGGTTCCCTTACGAGGGC
CCAGCTCCCCTGGAAGCTATCGCAAATGGATGTGCTTTTCTGAATCCCAAGTTCAACCCACCCAAAAGCAGCAAAACAC
AGACTTTTCATTGGCAAGCCAACTCTGAGAGAGCTGACATCCCAGCATCCTTACGCTGAAGTTTTCATCGGCGGCCAC
ATGTGTGGACTGTTGACCTCAACAATCAGGAGGAATCAGGAGGATGCAGTAGAGGATGCAGTAGCAATTTAAATCAGAAGATTGAGCCA
TACATGCCATATGACATTTACGTGCGAGGGATGCTACAGAGAATCAATGCTTTCATTGAAAAACAGGACTTCTGCCATGG
GCAAGTGATGTGGCCACCCCTCAGCGCCCTACAGTTGCTGAGCCGGCAGTCTGCAAGCAGCATGCCAGTGTGCCAGG
AGAGCCAGTCATCTGCGAGCTTCTCTTCCAGCACCTCAACAAGGACAAGGACATGCGAAGTACAAGGTGACCTGC
CAAAGCTCAGAGCTGGCCAAGGACATCCTGGTGCCCTCCTTGGTCGTGTTTCAAGGTGACCT
CCTGCTCTTCAGCTGTGCAGGCCGCGCCACCCAGCACCAGAGGCCCTGCCCTGCCCTCATCAAGGCCAGGTGG
CTCTCTGCAAAGACTGCCTATAGCAGCTACCTGCTCAGCCCTGCCACCATGCTGCTGGGGAAGACAGTGGCCCCAGCCACA
*TCAGGGAGGACCAT*

Lower case:          terminal part of intron "I" of GnT-V gene.
Lower case:      sequence coding for the peptide.
UPPER CASE:          sequence homologous to GnT-V cDNA (nucleotides 1676 to 2421)
UPPER CASE:      exon "B" of GnT-V
*ITALICS:*           end OF 3'; RACE clone, complementary to primer VB72 used in PCR.

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 2237
        ( B ) TYPE: nucleic acid
        ( C ) STRANDEDNESS: single
        ( D ) TOPOLOGY: linear ( x i ) SEQUENCE DESCRIPTION: SEQ ID NO: 1:

| | | | | | | |
|---|---|---|---|---|---|---|
| GCCGCCTGCA | AGCTAGGAAT | GCCCGTCCTG | CCTGATGGTC | CTGCCTGATG | TGTTCATACG | 60 |
| CTGTGTGGTT | TTCTGTCTTA | CAGTTGTTTG | TTGGACTTGG | GTTCCCTTAC | GAGGGCCCAG | 120 |
| CTCCCTGGA | AGCTATCGCA | AATGGATGTG | CTTTTCTGAA | TCCCAAGTTC | AACCCACCCA | 180 |
| AAAGCAGCAA | AAACACAGAC | TTTTTCATTG | GCAAGCCAAC | TCTGAGAGAG | ATAAATTTGC | 240 |
| GCCTCATTTT | GGTAAGCGGA | AAAACAAAAG | AGTTCCTGTT | TTCTCCTAAC | GATTCTGCTT | 300 |
| CTGACATTGC | AAAGCATGTA | TATGACAATT | GGCCAATGGA | CTGGGAAGAA | GAGCAGGTCA | 360 |
| GCAGTCCAAA | TATTCTACGA | CTTATTTATC | AAGGACGATT | TCTACATGGA | AATGTCACAT | 420 |
| TAGGAGCATT | AAAACTTCCT | TTTGGCAAAA | CAACAGTGAT | GCATTGGTG | GCCAGAGAGA | 480 |
| CATTACCAGA | GCCAAACTCT | CAAGGTCAGA | GGAATCGTGA | GAAGACTGGA | GAGAGTAATT | 540 |
| GTTGTGTAAG | CTGTAAACAC | TGTCTGCCTA | GTGTGATGTG | ATATAGTCTT | TGTCTTTCAT | 600 |
| GCTGCTGGAC | AGAAAAGACC | CGACATTGCT | TCAGAAACCG | TTCAGAACAG | TCTGCCTGTA | 660 |
| AACACATGGA | ACTGAATTAC | CACATGAACA | CTGTCATCTT | TTGCTCATGA | AAGTAAAAAG | 720 |
| AACCAAGAAC | ATTTTTCACT | CTGATTTTTT | ATTTCTTGTA | TTTTTGTTG | AGCTGTTTTA | 780 |
| ACACATATTG | GTTTTTGAAT | GCAGTCAATC | TCCAGGGGAA | AAGTTAACAA | GTTATCTTTC | 840 |
| GTAGCAGAAA | CCATTTTGCT | GCCACAAAAT | TTTCATCATC | AGAACTAATA | AATCAAGTGT | 900 |
| TCCAAATACA | ATTTGCACTA | AAAAGATTGG | CATTATTTTC | CTCATCAGCA | GAATTTATAA | 960 |
| CAGTGTGTGG | TATCTAGAAA | TACTTATATA | TACAATTCCA | CACTGGAAGA | CACTCAGCAA | 1020 |
| TTAATGAAGT | TAATTACTGG | GCCAACTTGA | GACCAAAAAA | TGGAAAAGAA | ACTAAATGT | 1080 |
| TGGGTGAATT | CTACCAAAGT | CAGCCGTGGT | GGCTGCACTG | GCACAGAATA | CTAAACTGAG | 1140 |
| TGTGACTATT | TTCACTGCAA | CAAATGAAAA | AACAAATGT | GCCTGTTTAA | AGCACTCAGT | 1200 |
| AGAGGGCTGA | TGAAACTAAT | TTTTTTTCCT | TTAAGACATG | CACTCTTGAG | TCCTACAGTA | 1260 |
| ACTGAGTGTT | TGTTTAGACA | GCACAAGAAG | GGGTGAGAGT | GCGTCTCCTA | GCCTTAATGT | 1320 |
| GGGAGGGTAG | TTTCAGTCAC | TCATCGGCTT | TCATTATTGT | GCAGAAATAT | TAGAAAACCT | 1380 |
| CATTGATCAA | TTTTATGTAT | TTGAATATCA | GCAAATTGAA | ATTTTCCATA | ATTATCATTA | 1440 |
| ATTTGTAACC | ACATCCAGTG | TCATGCTTAC | TCCTTAGAGT | TCAGATGAAT | TCTTAAAATT | 1500 |
| AAAAAAAAG | TCCATAGTAC | TAATTTTGTT | TCTTTATATA | GTTGCGTTT | GATATTAGTG | 1560 |
| CTTGCAATTG | TATTAAAGTG | AAAAGCTCAT | TTTTATGGCA | TACACAAGAA | TGCCACTTTT | 1620 |
| TCTTTTATTT | CATACCAATA | ATTTAAAGAT | TGATATGCTA | AAAACAATTT | GCACAGCACT | 1680 |
| AAAGCATGAG | CTACTTTCAT | CTAAACCTGT | AAAAATATGA | AAGATTTTA | TATTTTTCA | 1740 |
| CTGGGAAGAA | ATTCTTCCTG | GATGAAATTA | CAAATATGTG | TAGAATATAT | TTAATAAAAG | 1800 |
| ACTTATAAAA | TACCTAACTA | CAGGACTTAA | AATATAGATT | GGCGCGTAGT | ATATAGAACA | 1860 |
| ATATTCCATA | TAAATAAGTT | TAGCCTTTAT | AAAAATGAAG | TTGCAGGCTA | GACATTACAT | 1920 |
| TCTGTACTTA | CTAAGTGTCA | ACAGCCCTTA | CAAACATTAA | ATGTAAATGG | TTTCAAATGG | 1980 |
| TCAGCGTGTT | AATGTAATCA | TGTTATTTTA | TTCATTGTTA | ATGCTTTGAT | GAAAGGCTT | 2040 |
| TATATGCAGT | AGATCTACGA | AAATATTGTT | CATACTGATC | AGAATTAAAT | TTGTATAGAG | 2100 |
| CAGAGTTTTA | AAATGAATGT | AAATAGCACT | AAACGTTTTC | TTTCTGCAAC | CTGTACTTAC | 2160 |
| AGATTCTTCC | TGTAAACTAA | ATAAAAAAAA | ATGATAGTAA | AAAAAAAAA | AAAAAAAAA | 2220 |
| AAAAAAAAAA | AATTCCT | | | | | 2237 |

( 2 ) INFORMATION FOR SEQ ID NO: 2:

( i ) SEQUENCE CHARACTERISTICS:

( A ) LENGTH: 18
( B ) TYPE: nucleic acid
( C ) STRANDEDNESS: single
( D ) TOPOLOGY: linear ( x i ) SEQUENCE DESCRIPTION: SEQ ID NO: 2:

ACTGCTTACT GGCTTATC                                                                                              18

( 2 ) INFORMATION FOR SEQ ID NO: 3:

( i ) SEQUENCE CHARACTERISTICS:
( A ) LENGTH: 26
( B ) TYPE: nucleic acid
( C ) STRANDEDNESS: single
( D ) TOPOLOGY: linear ( x i ) SEQUENCE DESCRIPTION: SEQ ID NO: 3:

TCAGCTTTTG GGTGGGTTGA ACTTGG                                                                                     26

( 2 ) INFORMATION FOR SEQ ID NO: 4:

( i ) SEQUENCE CHARACTERISTICS:
( A ) LENGTH: 24
( B ) TYPE: nucleic acid
( C ) STRANDEDNESS: single
( D ) TOPOLOGY: linear ( x i ) SEQUENCE DESCRIPTION: SEQ ID NO: 4:

GCCGCCATGG TCCTGCCTGA TGTG                                                                                       24

( 2 ) INFORMATION FOR SEQ ID NO: 5:

( i ) SEQUENCE CHARACTERISTICS:
( A ) LENGTH: 34
( B ) TYPE: nucleic acid
( C ) STRANDEDNESS: single
( D ) TOPOLOGY: linear ( x i ) SEQUENCE DESCRIPTION: SEQ ID NO: 5:

CTAGTGTAAG ACAGAAAACC ACACAGCGTA TGAA                                                                            34

( 2 ) INFORMATION FOR SEQ ID NO: 6:

( i ) SEQUENCE CHARACTERISTICS:
( A ) LENGTH: 10
( B ) TYPE: amino acid
( C ) STRANDEDNESS: single
( D ) TOPOLOGY: linear ( x i ) SEQUENCE DESCRIPTION: SEQ ID NO: 6:

Val Leu Pro Asp Val Phe Ile Arg Cys Val
                  5                   10

( 2 ) INFORMATION FOR SEQ ID NO: 7:

( i ) SEQUENCE CHARACTERISTICS:
( A ) LENGTH: 9
( B ) TYPE: amino acid
( C ) STRANDEDNESS: single
( D ) TOPOLOGY: linear ( x i ) SEQUENCE DESCRIPTION: SEQ ID NO: 7:

Phe Ile Arg Cys Val Val Phe Cys Ile
                  5

( 2 ) INFORMATION FOR SEQ ID NO: 8:

( i ) SEQUENCE CHARACTERISTICS:

(A) LENGTH: 9
                (B) TYPE: amino acid
                (C) STRANDEDNESS: single
                (D) TOPOLOGY: linear (xi) SEQUENCE DESCRIPTION: SEQ ID NO: 8:

Val Leu Pro Asp Val Phe Ile Arg Cys
                5

(2) INFORMATION FOR SEQ ID NO: 9:

(i) SEQUENCE CHARACTERISTICS:
                (A) LENGTH: 8
                (B) TYPE: amino acid
                (C) STRANDEDNESS: single
                (D) TOPOLOGY: linear (xi) SEQUENCE DESCRIPTION: SEQ ID NO: 9:

Val Leu Pro Asp Val Phe Ile Arg
                5

(2) INFORMATION FOR SEQ ID NO: 10:

(i) SEQUENCE CHARACTERISTICS:
                (A) LENGTH: 22
                (B) TYPE: nucleic acid
                (C) STRANDEDNESS: single
                (D) TOPOLOGY: linear (xi) SEQUENCE DESCRIPTION: SEQ ID NO: 10:

GGTTTCTCGA AGAAGGAACT GC                                                    22

(2) INFORMATION FOR SEQ ID NO: 11:

(i) SEQUENCE CHARACTERISTICS:
                (A) LENGTH: 21
                (B) TYPE: nucleic acid
                (C) STRANDEDNESS: single
                (D) TOPOLOGY: linear (xi) SEQUENCE DESCRIPTION: SEQ ID NO: 11:

CAGCGTATGA ACACATCAGG C                                                     21

(2) INFORMATION FOR SEQ ID NO: 12:

(i) SEQUENCE CHARACTERISTICS:
                (A) LENGTH: 18
                (B) TYPE: nucleic acid
                (C) STRANDEDNESS: single
                (D) TOPOLOGY: linear (xi) SEQUENCE DESCRIPTION: SEQ ID NO: 12:

AGGACCATCA GGCAGGAC                                                         18

(2) INFORMATION FOR SEQ ID NO: 13:

(i) SEQUENCE CHARACTERISTICS:
                (A) LENGTH: 22
                (B) TYPE: nucleic acid
                (C) STRANDEDNESS: single
                (D) TOPOLOGY: linear (xi) SEQUENCE DESCRIPTION: SEQ ID NO: 13:

CACTATGCTC TCCTCCACCA AG                                                    22

(2) INFORMATION FOR SEQ ID NO: 14:

(i) SEQUENCE CHARACTERISTICS:

(A) LENGTH: 35
(B) TYPE: nucleic acid
(C) STRANDEDNESS: single
(D) TOPOLOGY: linear (xi) SEQUENCE DESCRIPTION: SEQ ID NO: 14:

GACTCGAGTC GACATCGATT TTTTTTTTTT TTTTT                              35

(2) INFORMATION FOR SEQ ID NO: 15:

(i) SEQUENCE CHARACTERISTICS:
(A) LENGTH: 18
(B) TYPE: nucleic acid
(C) STRANDEDNESS: single
(D) TOPOLOGY: linear (xi) SEQUENCE DESCRIPTION: SEQ ID NO: 15:

ATGGTCCTGC CTGATGTG                                                 18

(2) INFORMATION FOR SEQ ID NO: 16:

(i) SEQUENCE CHARACTERISTICS:
(A) LENGTH: 23
(B) TYPE: nucleic acid
(C) STRANDEDNESS: single
(D) TOPOLOGY: linear (xi) SEQUENCE DESCRIPTION: SEQ ID NO: 16:

GATGTGTTCA TACGCTGTGT GGT                                           23

(2) INFORMATION FOR SEQ ID NO: 17:

(i) SEQUENCE CHARACTERISTICS:
(A) LENGTH: 1054
(B) TYPE: nucleic acid
(C) STRANDEDNESS: single
(D) TOPOLOGY: linear (xi) SEQUENCE DESCRIPTION: SEQ ID NO: 17:

ATCCTCCCTA CCCCGTGATA CCCCTAGACA CTAATTTTTT AGTTCCTTGG TGGAGGAGAG    60

CATAGTGAGT TGAGCAGCTT TGTGGGACTT TAAAAGTTCG TAGTTTTTCA GATCCTGGTG   120

TAAGCTGAAT TCTCTCTGCC CCACCCCCA GGGCCTGGGA GCCTTCCAAA GTGAGGTGTC    180

CACACGGGAA TGGGCCACAG AATCGCCGCC TGCAAGCTAG GAATGCCCGT CCTGCCTGAT   240

GGTCCTGCCT GATGTGTTCA TACGCTGTGT GGTTTTCTGT CTTACAGTTG TTTGTTGGAC   300

TTGGGTTCCC TTACGAGGGC CCAGCTCCCC TGGAAGCTAT CGCAAATGGA TGTGCTTTTC   360

TGAATCCCAA GTTCAACCCA CCCAAAAGCA GCAAAAACAC AGACTTTTC ATTGGCAAGC    420

CAACTCTGAG AGAGCTGACA TCCCAGCATC CTTACGCTGA AGTTTTCATC GGGCGGCCAC   480

ATGTGTGGAC TGTTGACCTC AACAATCAGG AGGAAGTAGA GGATGCAGTG AAAGCAATTT   540

TAAATCAGAA GATTGAGCCA TACATGCCAT ATGAATTTAC GTGCGAGGGG ATGCTACAGA   600

GAATCAATGC TTTCATTGAA AAACAGGACT TCTGCCATGG GCAAGTGATG TGGCCACCCC   660

TCAGCGCCCT ACAGGTCAAG CTTGCTGAGC CCGGGCAGTC CTGCAAGCAG GTGTGCCAGG   720

AGAGCCAGCT CATCTGCGAG CCTTCTTTCT TCCAGCACCT CAACAAGGAC AAGGACATGC   780

TGAAGTACAA GGTGACCTGC CAAAGCTCAG AGCTGGCCAA GGACATCCTG GTGCCCTCCT   840

TTGACCCTAA GAATAAGCAC TGTGTGTTTC AAGGTGACCT CCTGCTCTTC AGCTGTGCAG   900

GCGCCCACCC CAGGCACCAG AGGGTCTGCC CCTGCCGGGA CTTCATCAAG GGCCAGGTGG   960

CTCTCTGCAA AGACTGCCTA TAGCAGCTAC CTGCTCAGCC CTGCACCATG CTGCTGGGGA  1020

-continued

```
AGACAGTGGC CCCAGCCACA TCAGGGAGGA CCAT                                    1054
```

( 2 ) INFORMATION FOR SEQ ID NO: 18:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 18:

```
GGCATCGTGA TGGACTCCG                                                     19
```

( 2 ) INFORMATION FOR SEQ ID NO: 19:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 19:

```
GTCGGAAGGT GGACAGCGA                                                     19
```

ISOLATED NUCLEIC ACID MOLECULES, PEPTIDES WHICH FORM COMPLEXES WITH MHC MOLECULE HLA-A2 AND USES THEREOF

FIELD OF THE INVENTION

This invention relates to isolated nucleic acid molecules and peptides which are useful in connection with the diagnosis and treatment of pathological conditions. More particularly, it relates to a protein which is processed to peptides presented by the MHC molecule HLA-A2, and the presented peptides themselves. These peptides are useful in diagnosis and therapeutic contexts.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See Male et al., *Advanced Immunology* (J.P. Lipincott Company, 1987), especially chapters 6–10. The interaction of T cells and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See Barinaga, *Science*, 257: 880 (1992); Fremont et al., *Science*, 257: 919 (1992); Matsumura et al., *Science*, 257: 927 (1992); and Latron et al., *Science*, 257: 964 (1992).

The mechanism by which T cells recognize cellular abnormalities has also been implicated in cancer. For example, in PCT application PCT/US92/04354, filed May 22, 1992, published on November 26, 1992, and incorporated herein by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics*, 35: 145 (1992); van der Bruggen et al., *Science*, 254: 1643 (1991), for further information on this family of genes. Also, see U.S. Pat. No. 5,342,774.

In U.S. patent application Ser. No. 938,334, the disclosure of which is incorporated herein by reference, nonapeptides are taught which are presented by the HLA-A1 molecule. The reference teaches that given the known specificity of particular peptides for particular HLA molecules, a particular peptide is expected to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

As described hereinbelow, the present application is directed to new intron-expressed tumor rejection antigens which are presented by MHC molecule HLA-A2, and to nucleic acid molecules encoding said antigens. The present application is further directed to therapeutic and diagnostic methods utilizing the new tumor rejection antigens. The invention is elaborated upon further in the disclosure which follows.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 6 represents the nucleotide sequences for the 5' and 3' extremities of a 14 kb insert of genomic DNA from MZ2-MEL2.2.5, in λ phage. This 14 kb insert was positive when screened with a probe corresponding to nucleotides 48–185 of cDNA 560E1;

FIG. 9 represents a compilation of nucleic acid sequences of the longest 5' RACE clone and the 3' RACE clone.

EXAMPLE 1

Figure 1:
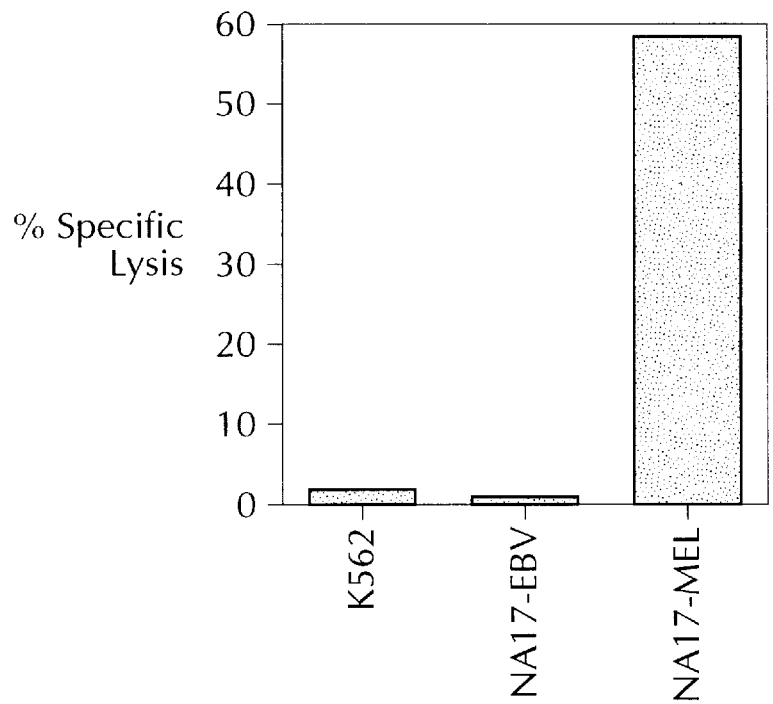
FIG. 1 shows $^{51}$Cr release by NA17-MEL, NA17-EBV and K562 cells when incubated with CTL 213.

Tumor cell lines utilized herein were obtained as follows: cell lines NA8-MEL, NA17-MEL and NA74-MEL were derived from the metastatic melanomas of patients NA8, NA17 and NA74. The melanoma cells NA17-MEL and NA74-MEL were obtained from patients NA17 and NA74 and cultured in RPMI 1640 supplemented with 10% FCS, 1% penicillin-streptomycin and 1% L-glutamine. Subline MZ2-MEL.43 was derived from melanoma cell line MZ2-MEL and cultured as previously described by Herin, et al., *Int. J. Cancer*, 39:390–396 (1987) and Van den Eynde et al., *Int. J. Cancer*, 44:634–640 (1989). Melanoma cell lines SK29-MEL and SK23-MEL were provided by Dr. Lloyd Old, and are well known. The culture medium for SK29-MEL, SK23-MEL and NA8-MEL has been previously described (Coulie et al., *J. Exp. Med.*, 18:35–42 (1994)). Tumor cell line LB373-MEL was derived from melanoma patient LB373 and cultured in Iscove medium supplemented in 10% FCS. Lymphoblastoid cells NA17-EBV (B cells transformed with Epstein Barr Virus) were derived from patient NA17 by standard techniques and were cultured in RPMI 1640 supplemented with 10% FCS, 1% penicillin-streptomycin and 1% L-glutamine.

Cytolytic T cell line CTL 213 was obtained by culturing fragments of cutaneous metastatic melanoma of patient NA17 in IL-2 supplemented medium as described by Pandolfino et al., *Eur. J. Immunol.*, 22:1795–1802 (1992), which is incorporated herein by reference. Specifically, fragments of cutaneous metastatic melanoma M17 were cultured with IL-2 supplemented medium consisting of RPMI 1640, 8% human AB serum, 150 U/ml of recombinant interleukin-2 (rIL-2) and antibiotics. This type of culture resulted in a mixed lymphocyte-tumor cell culture (MLTC). CTLs were cultured for 16 days before cloning.

Limiting dilution culture of CTLs was then carried out in 96-well microplates at 0.3, 0.6, 3, 6 and 30 CTL/well together with irradiated feeder and stimulator cells ($2 \times 10^4$ LAZ cells and $1.5 \times 10^3$ melanoma cells) in 200 $\mu$l rIL-2 medium containing phytohemagglutinin (PHA) (1/1000). After 48 hours, and then twice weekly, half a volume of each well was replaced by fresh IL-2 medium. After 15 to 20 days of culture, each well was scored microscopically for growth. Microcultures showing a probability of being clonal superior to 80% were transferred into new plates with freshly irradiated feeder and stimulator cells. Long-term clone growth was obtained by similarly transferring $2 \times 10^3$ or $5 \times 10^3$ lymphocytes/well every 2 or 3 weeks. One of the CTL clones obtained was denoted CTL 213. Viret et al., *Eur. J. Immunol.*, 23:141–146 (1993) teach that CTL 213 lysed 12 of 15 melanoma cell lines tested via a cell lysis assay. This CTL was used in the experiments which follow.

EXAMPLE 2

Autologous cells of the cell line NA17-MEL were mixed with CTL 213 to determine whether or not CTL 213 recognized an antigen presented on the melanoma cell line. The assay used was the well known $^{51}$Cr release assay, as described by Hérin et al., *Int. J. Cancer*, 39:390–396 (1987), which is incorporated herein by reference. The assay, however, is described herein. The target melanoma cells were grown in vitro, and then resuspended at $10^7$ cells/ml in RPMI 1640, supplemented with 10% FCS, and incubated for 45 minutes at 37° C. with 200 $\mu$Ci/ml of Na($^{51}$Cr)O$_4$. Labelled cells were washed three times with RPMI 1640, supplemented with 10% FCS. These were then resuspended in RPMI 1640 supplemented with 10% FCS, after which 100 $\mu$l aliquots containing $10^3$ cells, were distributed into 96 well microplates. Samples of CTL 213 were added in 100 $\mu$l of the same medium, and assays were carried out in duplicate. Plates were incubated for four hours at 37° C. in a 8% CO$_2$ atmosphere.

Plates were centrifuged and 100 $\mu$l aliquots of supernatant were collected and counted. Percentage of $^{51}$Cr release was calculated as follows:

$$\% \; ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 $\mu$l of medium alone, and MR is maximum release, obtained by adding 100 $\mu$l 0.3% Triton X-100 to target cells.

The NA17-MEL cells (target cells, or "T") were mixed with cells of CTL 213 ("effector cells" or "E"), at an E/T ratio of 10:1. Also tested were natural killer cells (cell line K562), and autologous EBV-transformed-$\beta$ cells ("NA17-EBV"). $^{51}$Cr release was measured after four hours, and the results are shown in FIG. 1. They indicate that CTL 213 recognized a peptide/MHC complex on the surface of the NA17-MEL cells. CTL 213 did not lyse either K562 or autologous EBV-B cells, thus indicating that the gene coding for the pertinent antigen was expressed only in the NA17 cells.

EXAMPLE 3

The MHC molecule which presents the antigen for which CTL 213 is specific was determined by lysis inhibition, using two anti-HLA-A2 monoclonal antibodies (mAbs), described by Viret et al., supra. Antibodies used were obtained from hybridomas PA2.1 (anti-A2/A28) and MA2.1 (anti-A2/B17). These mAbs are representative of a large number of HLA-A2 specific mAbs, known to the art. Inhibition by mAbs of cytolysis by CTL 213 was assayed on NA17 tumor cells (referred to as M17 in Viret et al., supra) treated with 200 U/ml recombinant interferon $\alpha$ (rIFN-$\alpha$) for 48 hours. Lysis was inhibited in a dose-dependent manner by anti-A2/A28 and anti-A2/B17 antibodies, which indicates that the presenting molecule for the antigen is HLA-A2.

EXAMPLE 4

Figure 2:
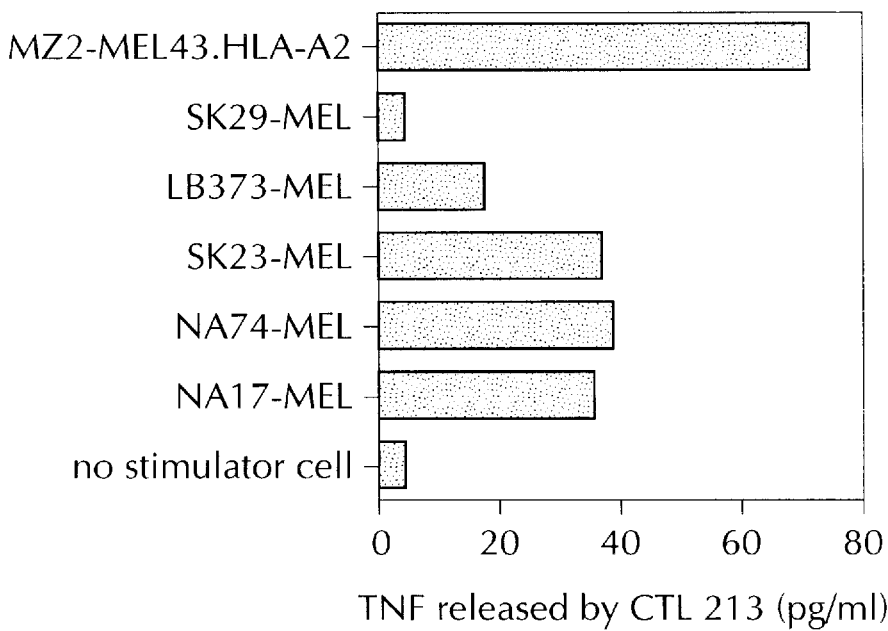
FIG. 2 shows TNF release when cytolytic T cell line CTL 213 is contacted with cell lines MZ2-MEL 43.HLA-A2, SK29-MEL, LB373-MEL, SK23-MEL, NA74-MEL and NA17-MEL.

Additional experiments were carried out with CTL 213, using allogeneic melanoma cell lines previously identified as presenting HLA-A2 on their surface. The assay used was a TNF release assay, as described by Traversari et al., *Immunogenetics*, 35:135–142 (1992), and incorporated herein by reference. Briefly, to determine TNF release, 2500 cells of CTL 213 were added in 100 $\mu$l of RPMI 1640 medium containing 10% human serum and 25 units/ml r-hu-IL2 to microwells containing target cells. After 48 hours, the supernatant was collected and its TNF content was determined by testing its cytotoxic effect on WEHI-164 clone 13 cells. The target allogeneic cell lines were SK29-MEL, LB 373-MEL, SK23-MEL, NA74-MEL, and MZ2-MEL 43.HLA-A2. As shown in FIG. 2, four out of five lines were positive, and the allogeneic line MZ2-MEL43.HLA-A2 ("MEL.43" hereafter) provided better results than NA17-MEL. For this reason, MEL.43 was used in the experiments which follow. It is to be noted that MEL.43 does not present HLA-A2 naturally, but has been transfected with a vector containing the gene which codes for HLA-A2.

EXAMPLE 5

Once the presenting HLA molecule was identified as HLA-A2, studies were carried out to characterize the peptide/MHC complex further. The first step involved the identification of the molecule which was processed to the peptide.

To do this, Poly-A+ RNA was extracted from MZ2-MEL.43 cells using an mRNA extraction kit. The mRNA was converted to CDNA using an oligo dT (NotI, EcoRI) primer, ligated to BstXI adaptors as described in the Super-Script plasmid system kit (Gibco BRL), digested with NotI, and inserted into the BstXI/NotI site of expression vector pcDNAI/AMP following the manufacturer's (Invitrogen Corp.) instructions. Recombinant plasmids were electroporated into DH5α Escherichia coli bacteria and selected with ampicillin (50 μg/ml).

The transfected bacteria were divided into 647 pools of 100 bacteria. Each pool represented about 90 different cDNAs, as analysis showed that about 90% of plasmids contained an insert. Each pool was amplified to saturation, and plasmid DNA was isolated via alkaline lysis, potassium acetate precipitation and phenol extraction, following Maniatis et al., in *Molecular Cloning: A Laboratory Manual* (Cold Spring Harbor, N.Y. 1982). Cesium gradient centrifugation was not used.

The amplified plasmids were then co-transfected into eukaryotic cells with plasmid pcDNAI-Amp-A2 which contained the gene coding for HLA-A2. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, 100 ng of plasmid pcDNA-I/Amp-A2 and 100 ng of DNA of a pool of the cDNA library described supra. Following four hours of incubation at 37° C., the medium was removed, and replaced by 50 μl of PBS containing 10% DMSO. This medium was removed after two minutes and replaced by 200 μl of DMEM supplemented with 10% FCS.

Following this change in medium, COS cells were incubated for 48 hours at 37° C. Medium was then discarded, and 2500 cells of CTL 213 were added in 100 μl of RPMI 1640 medium containing 10% pooled human serum, supplemented with 25 U/ml of IL-2. Supernatant was removed after 24 hours, and TNF content was determined in the TNF assay on WEHI-164 clone 13 cells, as described supra.

Of 647 wells tested in duplicate, most produced between 1 and 4 pg of TNF per ml. However, two pools produced duplicates which generated 4 and 8 and 5 and 6 μg/ml of TNF in the supernatants. In view of these results, these pools were used in another transfection.

EXAMPLE 6

To confirm these two putative positive pools, another transfection was done with these pools and with several other pools. One of the two putative positive pools remained clearly positive (10 and 9 pg/ml in the duplicates versus less than 3 pg/ml in the other microcultures).

Figure 3:
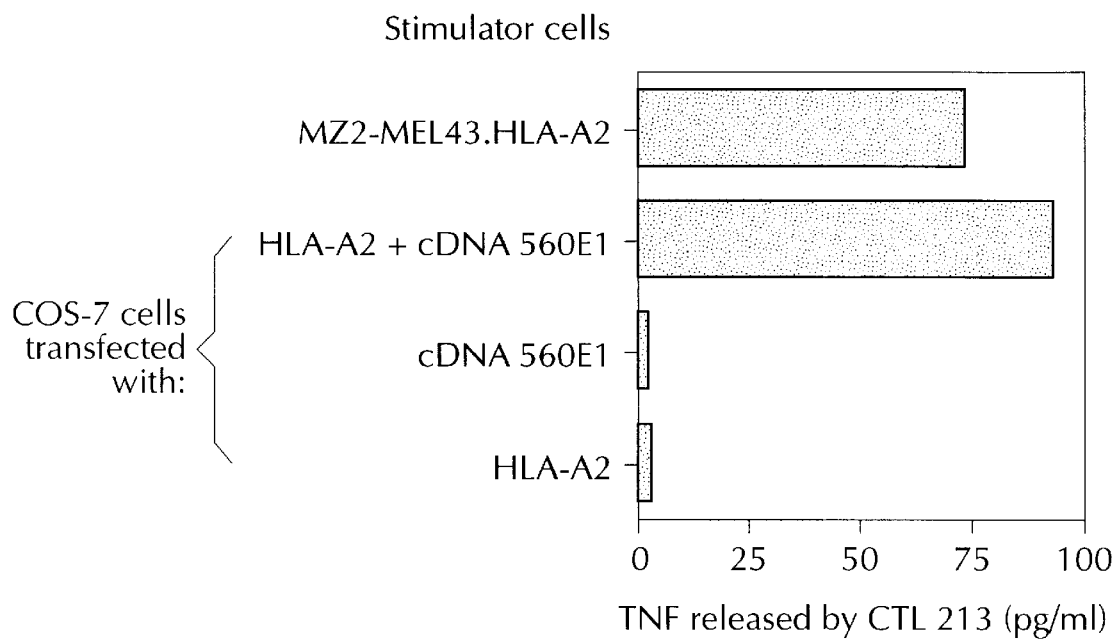
FIG. 3 shows TNF release when CTL 213 is contacted with MZ2-MEL.43 cells transfected with HLA-A2, COS-7 cells cotransfected with HLA-A2 and 560E1 cDNA, or COS-7 cells transfected with either HLA-A2 alone or 560E1 cDNA alone.

The bacteria of this positive pool were cloned, and 1150 bacteria were tested. Their plasmid DNA was extracted, cotransfected with the HLA-A2 construct described supra (pcDNA-Amp-A2) and the COS-7 cotransfectants were tested for their ability to stimulate CTL 213 in the manner described supra. Two positive clones were found in the positive pool. The results obtained with one of these cDNA clones (560E1) is shown in FIG. 3. FIG. 3 shows that TNF is released when CTL 213 is contacted with MZ2-MEL.43 cells transfected with HLA-A2. TNF is also released when CTL 213 is contacted with COS-7 cells cotransfected with HLA-A2 and 560E1 cDNA. No TNF is released when CTL 213 is contacted with either COS-7 cells transfected with HLA-A2 alone, or COS-7 cells transfected with 560E1 cDNA alone.

EXAMPLE 7 cDNA 560E1 was sequenced. DNA sequencing analysis was performed by specific priming with synthetic oligonucleotides. The sequencing reactions were performed using the dideoxy-chain termination method. A computer search for sequence homology, once the sequence was deduced, was done with programs FASTA@EMBL-Heidelberg and blast@ncbi.nlm.nih.gov.

cDNA 560E1 (SEQ ID NO: 1) is 2237 base pairs long. Comparison of the 560E1 sequence to sequences in the Gene Bank library revealed that nucleotides 84–230 of 560E1 were identical to a portion of cDNA coding for N-acetylglucosaminyltransferase V ("GnT-V") as described by Saito et al., *Biochem. Biophys. Res. Commun.*, 198:318 (1994). Upstream base pairs 1–83 of 560E1 showed no significant homology with any other sequences in the cDNA library, however, as will be discussed infra, region 1–83 is homologous to an intron of GnT-V.

EXAMPLE 8

Figure 4A:
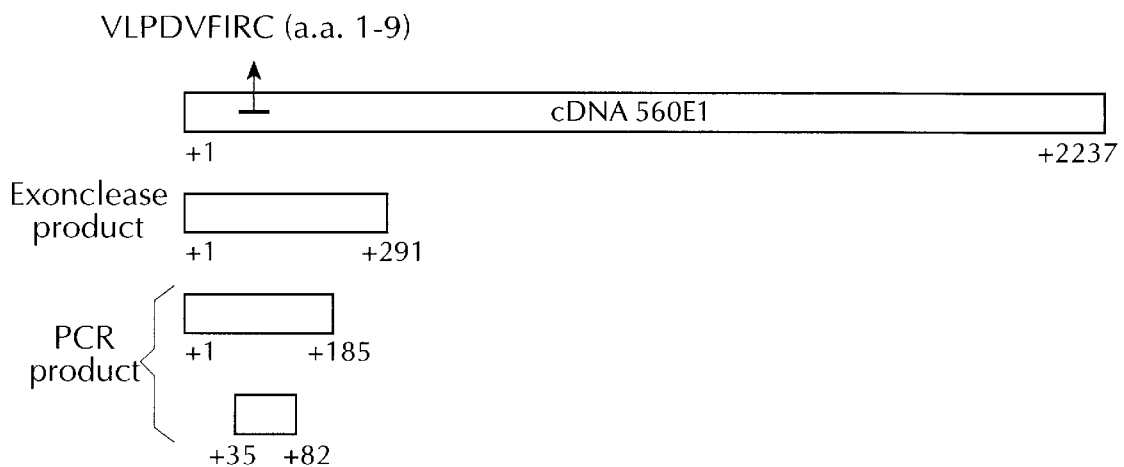
FIG. 4A shows the location of regions within cDNA 560E1 which code for the NAG antigenic peptides recognized by CTL 213.
Figure 4B:
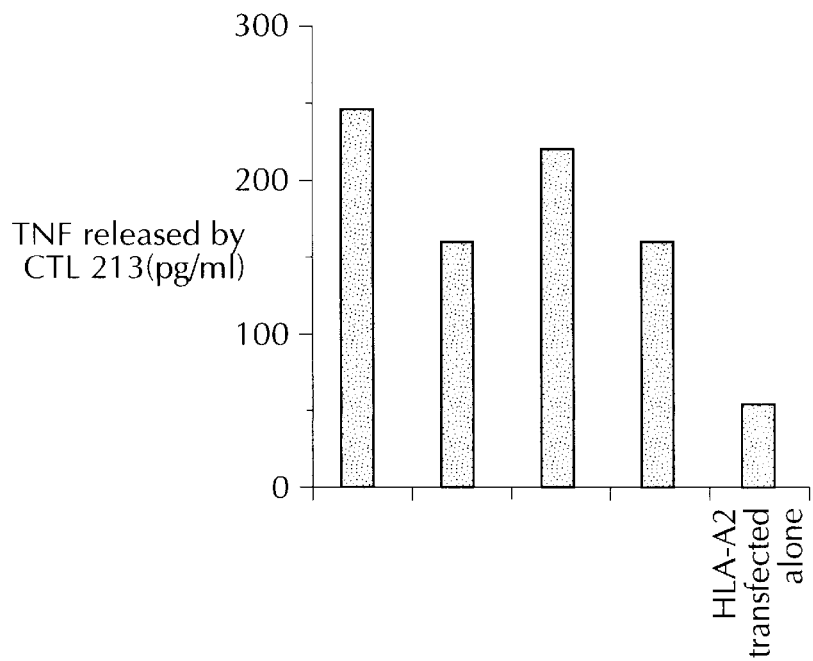
FIG. 4B shows TNF release after incubation of CTL 213 with COS cell cotransfectants of cDNA 560E1 fragments cloned into pcDNA I/Amp and HLA-A2.

To determine the antigens derived from 560E1 and presented by HLA-A2 (referred to herein as the "NAG antigens"), exonuclease digestion was carried out on cDNA 560E1, using standard techniques, to prepare cDNA fragments. To perform exonuclease digestion, the plasmid containing cDNA 560E1 was cleaved with NotI and SphI before digesting with exonuclease III. This treatment was performed with the Erase-a-Base® System (Promega, Madison, Wis.). After ligation, the plasmids were electroporated in TOP 10F' *Escherichia coli* bacteria and selected with ampicillin (50 μg/ml). Clones were isolated and plasmid DNA was extracted from each clone and transfected into COS-7 cells together with HLA-A2 gene. A region was identified which expressed the NAG antigen. The region spanned nucleotides 1–291 of SEQ ID NO: 1 (FIG. 4).

Various portions of this region (i.e., nucleotides 1–291) were amplified, using the polymerase chain reaction and standard techniques. Fragments were generated from cDNA clone 560E1 by PCR amplification. The ends were blunted and phosphorylated and the fragments were subcloned in vector pcDNAI/Amp digested with EcoRV. To generate PCR fragment 1–185, VB1 (5'-ACTGCTTACTGGCTTATC-3') (SEQ ID NO: 2) was used as sense primer (complementary to positions 2915 to 2932 of pcDNAI/Amp), and VB56 (5'-TCAGCTTTTGGGTGGGTTGAACTTGG-3') (SEQ ID NO: 3) was used as antisense primer (boundaries of PCR fragments are indicated as nucleotide positions relative to the first nucleotide of cDNA 560E1). To generate PCR fragment 35–82, VB72 (5'-GCCGCCATGGTCCTGCCTGATGTG-3') (SEQ ID NO: 4) was used as sense primer (note that the Kozak consensus sequence was added upstream of the ATG starting in position 35 of cDNA 560E1), and YG15 (5'-CTAGTGTAAGACAGAAAACCACACAGCGTATGAA-3') (SEQ ID NO: 5) was used as antisense primer.

This procedure identified a 48 base pair region (nucleotides 35 to 82) which was able to transfer expression of the antigen and which, in cotransfection experiments with the vector containing the HLA-A2 gene as described supra, led to lysis by CTL 213. The amino acid sequence coded for by this 48 base pairs sequence was then compared to a known HLA-A2 binding consensus sequence Xaa(Leu/Ile/Met)Xaa$_3$ZXaa$_2$(Val/Leu) where Z=Val, Leu, Ile, Thr (Falk et al., *Nature,* 351:290–296 (1991) and Ruppert et al., *Cell,* 74:929–937 (1993)). Two sequences very similar to the HLA-A2 consensus sequence were found in this 48 base pair region.

EXAMPLE 9

Figure 5:
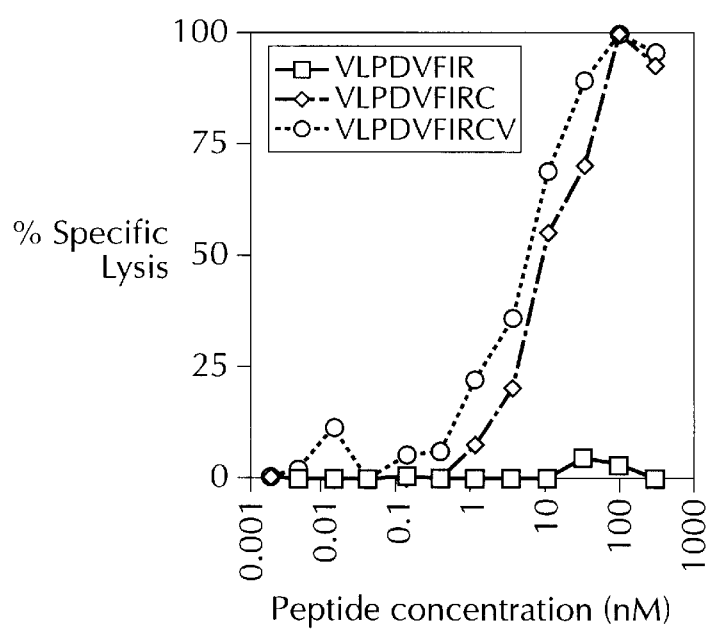
FIG. 5 shows lysis by CTL 213 of T2 cells expressing HLA-A2 incubated with various peptides.

The peptides encoded by these two sequences, Val Leu Pro Asp Val Phe Ile Arg Cys Val (SEQ ID NO: 6) and Phe Ile Arg Cys Val Val Phe Cys Ile (SEQ ID NO: 7) were synthesized and tested. Peptides were synthesized on solid phase using F-moc for transient NH2-terminal protection as described by Atherton et al., *J. Chem. Soc. Lond.,* 1:538 (1981) and characterized by mass spectrometry. All peptides were >90% pure as indicated by analytical HPLC. Lyophilized peptides were dissolved in DMSO and stored at −80°. They were tested by chromium release assay as described by Boon et al., *J. Exp. Med.,* 152:1184–1193 (1988). In this peptide sensitization assay, target cells were $^{51}$Cr-labeled for one hour at 37° C. and washed extensively. 1000 target cells were then incubated in 96-well microplates in the presence of various concentrations of peptide for 30 minutes at 37° C. before 10000 CTL 213 cells were added. Chromium release was measured after 4 hours at 37° C. Only 10-mer NAG antigen peptide Val Leu Pro Asp Val Phe Ile Arg Cys Val (SEQ ID NO: 6) (amino acids 1–10), corresponding to nucleotides 38–67, of 560E1 sensitized the target T2 cell line to CTL 213. Two nonameric peptides (amino acids 1–9 and amino acids 2–10) were synthesized and tested. NAG antigen nonapeptide Val Leu Pro Asp Val Phe Ile Arg Cys (SEQ ID NO: 8) (amino acids 1–9), corresponding to nucleotides 38–64, sensitized the target T2 cell line to CTL 213. Octapeptide Val Leu Pro Asp Val Phe Ile Arg (SEQ ID NO: 9) (amino acids 1–8) failed to confer any recognition (FIG. 5). When SEQ ID NO: 8 was compared to the exon for GnT-V given by Saito et al., supra, it was found that the peptide does not appear. It was also determined that the reading frame of SEQ ID NO: 1 differs from that of GnT-V.

EXAMPLE 10

Given the similarities between 560E1 cDNA and GnT-V-cDNA noted supra, additional studies were carried out to investigate the relationship, if any, between 560E1 CDNA and GnT-V cDNA.

First, a genomic library of MZ2-MEL.2.2.5 DNA in λ phage was prepared, using standard techniques. This library was probed with a $^{32}$p-labelled probe (probe "B") consisting of nucleotides 48–185 of 560E1 cDNA.

As a result of probing, a phage containing a 14 kilobase insert was identified. The insert was excised, and digested with SacI to yield a 5.5 kb fragment and an 8.5 kb fragment. These fragments were, in turn, probed with probe "B" used on the 14 kilobase insert, and with probe "A", a $^{33}$P-labelled oligonucleotide which has the sequence GGTTTCTCGAA-GAAGGAACTGC (SEQ ID NO: 10). The 8.5 kb fragment hybridized with probe B, and the 5.5 kb fragment with probe A. The two fragments were subcloned into plasmid pTZ19R and partially sequenced by well-known techniques.

It was found that the 8.5 kilobase fragment contained the first 83 nucleotides of 560E1 cDNA, which end with a splice donor site, followed by nucleotides 84–230, which are homologous to a part of GnT-V cDNA. This fragment is immediately followed by a splice donor site. Note that the first 83 nucleotides of 560E1 CDNA are not found in GnT-V CDNA.

Figure 7:
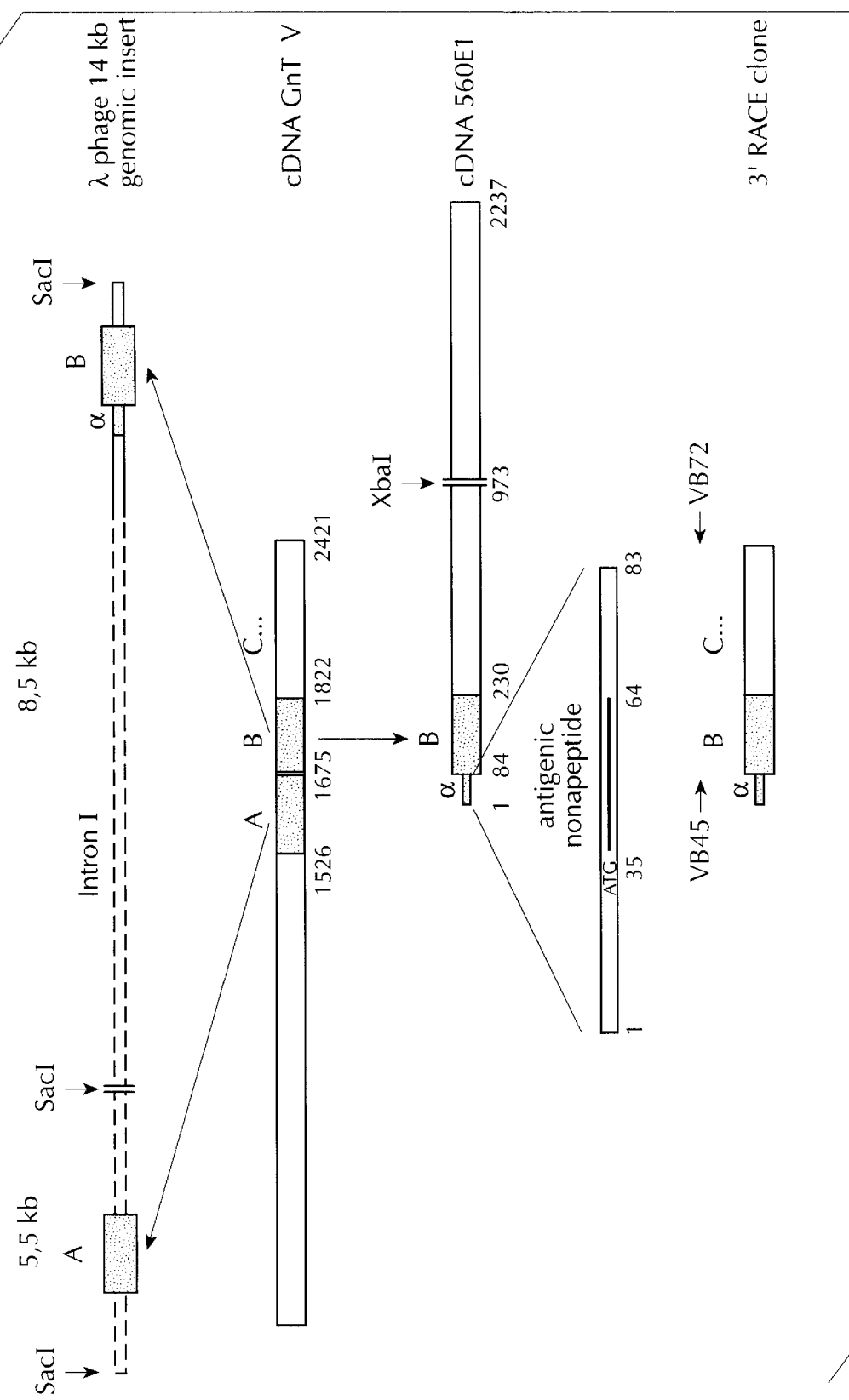
FIG. 7 is a schematic representation of cDNA 560E1, 3' RACE clone cDNA, GnT-V cDNA and X phage 14 kb genomic insert.

When the 5.5 kilobase fragment was sequenced, it was found to contain a 150 base pairs sequence which, when compared to GnT-V cDNA, was found to precede the sequence of bases 84–230 described supra. FIG. 7 shows this in some detail.

The 150 base pair and 147 base pair sequences represent two adjacent exons of GnT-V cDNA: exon A, found in the 5.5 kb fragment, comprises nucleotides 1526 to 1675 of GnT-V cDNA. Exon B, found in the 8.5 kb fragment, comprises nucleotides 1676 to 1822 of GnT-V cDNA. The sequence coding for the peptide is located in the terminal part of the intron comprised between GnT-V exons A and B (intron I in FIG. 7). This sequence belongs to an open reading frame which is different from the one coding for GnT-V.

EXAMPLE 11

A search for longer cDNAs which encode NAG tumor rejection antigen precursor in a cDNA library revealed that cDNA 560E1 is most likely a product of recombination between unrelated cDNAs. Specifically, colony hybridization studies, carried out with a probe corresponding to the 973 base pairs XbaI restriction fragment of cDNA 560E1 (FIG. 7) yielded several clones with 5' extremities which differ from cDNA 560E1 up to nucleotide 231, while 3' extremities were homologous to the 3' end of cDNA 560E1. As a result, the well known RACE (rapid amplification of cDNA ends) technique was used to search for the 3' extremity of the CDNA.

5' end amplification was performed using a 5'-Amplifinder™ RACE Kit (Clontech, Palo Alto, Calif.). The primer used for cDNA synthesis was YG104 (5'-CAGCGTATGAACACATCAGGC-3'), (SEQ ID NO: 11) nucleotide position 43 to nucleotide position 63 of cDNA 560E1). cDNA was ligated to Amplifinder™ anchor as described in the kit. A first round of PCR amplification was done with antisense primer YG104 and sense Amplifinder anchor primer described in the 5'-Amplifinder™ RACE Kit, and a second round of amplification with YG20 (5'-AGGACCATCAGGCAGGAC-3'), (SEQ ID NO: 12) nucleotide position 25 to nucleotide position 42 of cDNA 560E1) and the same AmpliFINDER anchor primer. The amplified product was cloned in the vector of pCR-Script™ SK(+) Cloning Kit (Stratagene, La Jolla, Calif.) and sequenced. Sequencing of the three cloned PCR products revealed sequences identical to the terminal part of intron I, however they were distinct from each other by their length: one clone starts 91 base pairs upstream exon B, another 199 base pairs upstream and the longest one 247 base pairs upstream. Clones obtained in the first experiment being relatively short and all of different sizes, 5' end amplification was performed in a second experiment using YG104 as a primer for cDNA synthesis, antisense primer YG20 (SEQ ID NO: 12) and sense AmpliFINDER anchor primer described in the Amplifinder RACE kit for a first round of PCR amplification and antisense primer YG31 (5'-CACTATGCTCTCCTCCACCAAG- 3') (SEQ ID NO: 13), located 161 nt 5' to YG20 in clones obtained in first experiment) and sense AmpliFINDER anchor primer for a second round of PCR amplification. Products were cloned as above. Eight cloned PCR products all shared the same sequence, identical to the terminal part of intron I, and starting 270 base pairs upstream exon B. In a third RACE experiment, an antisense primer located in exon B (VB56) (SEQ ID NO: 3) was used for reverse transcription, and rounds of amplification were performed with antisense primers YG104 and YG20 successively. Four cloned PCR products were sequenced. All were identical to the terminal part of intron I and started 96, 221, 234 and 287 base pairs upstream of exon B.

The intronic region that codes for the antigenic peptide may be available for translation as a result of the presence of partially unspliced GnT-V messenger in the cytosol. Alternatively, a promoter region located in the intron may be activated in some melanoma cells resulting in a messenger beginning in the last part of intron I. The inventors attempted to distinguish these possibilities by using RACE protocols to identify the 5' extremity of the messenger.

For 3' end amplification, the primer used for cDNA synthesis was EDP1260 (5'-GACTCGAGTCGACATCGATTTTTTTTTTTTTTTT-3' (SEQ ID NO: 14), described by Frohman et al., *Proc. Natl. Acad. Sci. USA,* 851:8998–9002 (1988). A first PCR amplification was done with sense primer VB72 (5'-ATGGTCCTGCCTGATGTG-3' (SEQ ID NO: 15), nucleotide position 35 to nucleotide position 52 of CDNA 560E1) and antisense primer EDP1260. A second PCR amplification was done with sense primer VB45 (5'-GATGTGTTCATACGCTGTGTGGT-3' (SEQ ID NO: 16), nucleotide position 47 to nucleotide position 69 of CDNA 560E1) and antisense primer EDP1260. The amplified product was cloned as above.

By rapid amplification of the 3' extremity with sense primers located in the first 83 nt of cDNA 560E1, and cloning of the amplified products, a cDNA clone was obtained whose sequence was homologous to the 3' end of GnT-V cDNA (from nucleotide 1675 to nucleotide 2421. This clone is referred to as 3' RACE clone. The sequence of antisense primer EDP1260, described supra, was used for cDNA synthesis and for PCR amplification. It was not found at the 3' end of this clone. Instead, the sequence of VB72, the primer used as sense primer in the first round of amplification, described supra, which had been used as antisense primer, was found.

To confirm that the 5' RACE results were not artifacts due to a putative localized secondary structure in the RNA molecule, a 1.3 kb HindIII-SacI restriction fragment of the 8.5 kb genomic subclone, containing exon B surrounded by intron sequences +/−900 base pairs upstream and 300 base pairs downstream, was cloned into transcription vector pGEM3Zf(-). Using SP6 RNA polymerase on SacI digested plasmid, the corresponding sense RNA was synthesized, treated with RNAse-free DNAseI, and diluted in irrelevant yeast tRNA. Two μg total RNA containing $1/10^2$, $1/10^4$ and $1/10^6$ relevant RNA were reverse transcribed with antisense primers VB56 or YG104. To evaluate plasmid DNA contamination, control reactions were set up without M-MLV-reverse transcriptase on the same RNA dilutions. PCR was performed on cDNAs with YG20 as antisense primer, and YG118 as sense primer. YG118 is located in intron I, 585 base pairs upstream of exon B. If no contaminating plasmid DNA persisted in RNA dilutions, a specific PCR product could only be obtained if cDNA synthesis was not interrupted by the putative localize secondary structure. Specific bands were indeed observed with cDNAs synthesized from $1/10^2$ and $1/10^4$ RNA dilutions, while no amplification could be detected on corresponding DNA contamination controls.

EXAMPLE 12

Figure 8:
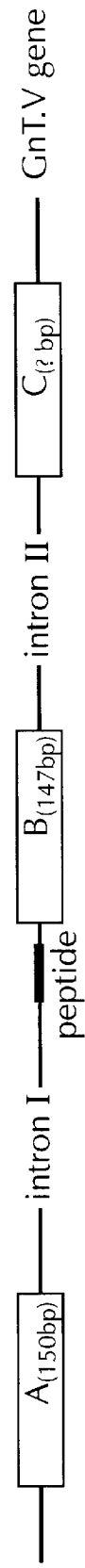
FIG. 8 is a schematic representation of part of the GnT-V gene.

Expression of GnT-V mRNA and NAG antigen in tissues and tumors was determined using PCR (see FIG. 8). In order to perform PCR, total RNA was extracted by the guanidine-isothiocyanate procedure as described by Davis et al., *Basic Methods in Molecular Biology,* Elsevier, N.Y., pp. 130–135 (1986). Reverse transcription was performed on 2 μg of total RNA in a reaction volume of 20 μl with 4 μl of 5 x reverse transcriptase buffer, 2 μl of a 20 mM solution of oligo(dT-15) primer, 20 U of RNasin, 2 μl of 0.1M dithiotreitol and 200 U of MoMLV reverse transcriptase. The reactants were incubated at 42° C. for 60 minutes.

For PCR, 1/200 of the CDNA reaction product was supplemented with 2.5 μl of 10 x thermostable DNA polymerase buffer, 0.5 μl each of 10 mM solutions of DNTP, 0.625 μl each of a 20 μM solution of primers, 0.5 U of DynaZyme™ and water to a final volume of 25 μl. For amplification of NA17-A cDNA (PCR "I-C"), VB45, (SEQ ID NO: 16) described supra, was used as sense primer, and YG28, consisting of nucleotide 1890 to nucleotide 1913 of GnT-V cDNA was used as anti-sense primer. For amplifications of GnT-V cDNA (PCR "A-B"), YG26, which consists of nucleotide 1538 to nucleotide 1561 of GnT-V cDNA, was used as sense primer, and YG29, which consists of nucleotide 1722 to nucleotide 1744 of GnT-V cDNA, was used as antisense primer. PCR was performed for 30 cycles (1 minute at 94° C., 2 minutes at 62° C. and 2 minutes at 72° C.). 10 μl of the PCR product was size-fractionated on a 1.5% agarose gel. The quality of RNA preparations was checked by PCR amplification of human β-actin cDNA with primers 5'-GGCATCGTGATGGACTCCG-3' (SEQ ID NO: 18) (exon 3 sense) and 5'-GTCGGAAGGTGGACAGCGA-3' (SEQ ID NO: 19) (exon 6 antisense) for 21 cycles of 1 minute at 94° C., 2 minutes at 65° C. and 2 minutes at 72° C.

For quantitative expression measurements, cDNA was synthesized as described supra. Pure RNA, obtained from clone MZ2-MEL.43, was included and serially diluted in each series of quantitative PCR. The number of cycles was reduced to 24 for PCR I-C, to 25 for PCR A-B and to 18 for β-actin PCR so that a linear curve of the standard was obtained. Trace amounts of labeled dCTP (0.2 μCi) were added and accurate quantitation was obtained using phosphor-imager technology.

PCR "A-B" amplified a 206 base pair-fragment from known GnT-V mRNA. All 22 normal tissue samples and all 29 melanoma samples tested by RT-PCR A-B were positive. RT-PCR "I-C" amplified a 271 base pair-fragment only from GnT-V transcripts that carried the terminal part of intron I and therefore coded for the NAG antigen.

A variety of normal tissues were tested by RT-PCR I-C (Table I). All 47 samples tested were negative except for a melanocyte cell line (level of expression of 60% of that observed in the MZ2-MEL.43 line) and one brain samples (out of 5 tested), and one breast sample (out of 6), which gave very slight bands. The brain sample giving the strongest band, and corresponding to a substancia nigra sample, was assayed by quantitative RT-PCR and revealed a level of expression of 4%. 13 HLA-A2 tumor cell lines were tested in parallel by quantitative RT-PCR I-C and in a TNF release assay with CTL 213. The 8 HLA-A2 tumor cell lines stimulating TNF release by CTL 213 had a level of expression of NAG antigen mRNA between 8% and 298% of that observed for the MZ2-MEL.43 cell line. The 5 HLA-A2 tumor cell lines which were negative in TNF assay showed levels of expression less than 3% of that observed in MZ2-MEL.43 cell line.

TABLE I

| Expression of NAG antigen and GnT-V in normal tissues | | |
|---|---|---|
| Type of Tissue | Number of positive results | % NA17-A Expression when determined |
| Adrenal gland | 0/3 | |
| Bladder | 0/4 | |
| Brain | 1/5 | 4% |
| Breast | 1/6 | 3% |
| Cerebellum | 0/1 | |
| Colon | 0/3 | |

TABLE I-continued

Expression of NAG antigen and GnT-V in normal tissues

| Type of Tissue | Number of positive results | % NA17-A Expression when determined |
|---|---|---|
| Epididyme | 0/2 | |
| Heart | 0/1 | |
| Kidney | 0/3 | |
| Liver | 0/3 | |
| Lung | 0/3 | |
| Marrow | 0/1 | |
| Muscle | 0/1 | |
| Ovary | 0/2 | |
| Prostate | 0/1 | |
| Scar | 0/2 | |
| Skin | 0/2 | |
| Stomach | 0/1 | |
| Testis | 0/3 | |
| Thymocytes | 0/1 | |
| Uterus | 0/1 | |
| Placenta | 0/1 | |
| Fetal testis | 0/1 | |
| Fetal brain | 0/4 | |

Forty-two melanoma tissue samples and 198 samples of tumors other than melanoma were tested by RT-PCR I-C. Samples giving PCR bands equivalent or stronger than that obtained with an eight fold dilution of reference MZ2-MEL.43 RNA (12.5%) were considered positive for NAG antigen expression. Those giving no detectable PCR band were considered negative. All samples giving PCR bands between 2% and 12.5% were considered intermediate assayed by quantitative RT-PCR in case of borderline result. Results are detailed in Table II, below. Half the melanoma samples expressed significant levels of NAG antigen, while most other types of tumor did not. (1 sarcoma and 1 brain tumor express significant levels of NAG antigen).

TABLE II

Expression of NAG antigen in tumor samples

| Type of Tumor | Number of samples tested | >12.5% | 2%–12.5% | >2% |
|---|---|---|---|---|
| Adrenal gland | 1 | 0 | 0 | 1 |
| Bladder | 15 | 0 | 0 | 15 |
| Brain | 10 | 1 | 2 | 7 |
| Breast | 25 | 0 | 2 | 23 |
| Colon-rectum | 10 | 0 | 4 | 6 |
| Head and neck | 15 | 0 | 0 | 15 |
| Kidney | 16 | 0 | 0 | 16 |
| Leukemia | 8 | 0 | 3 | 5 |
| Lung | 31 | 0 | 0 | 30 |
| Lymphoma | 2 | 0 | 0 | 2 |
| Melanoma | 42 | 20 | 9 | 13 |
| Neuroblastoma | 3 | 0 | 0 | 3 |
| Ovary | 1 | 0 | 0 | 1 |
| Pancreas | 4 | 0 | 1 | 3 |
| Prostate | 14 | 0 | 0 | 14 |
| Sarcoma | 22 | 1 | 2 | 19 |
| Skin | 3 | 0 | 0 | 3 |
| Stomach | 2 | 0 | 0 | 2 |
| Testis | 11 | 0 | 0 | 11 |
| Thymus | 1 | 0 | 0 | 1 |
| Thyroid | 1 | 0 | 0 | 1 |
| Uterus | 3 | 0 | 0 | 3 |

The foregoing examples show the isolation of a nucleic acid molecule which codes for an intron-expressed NAG tumor rejection antigen precursor. One aspect of the invention is an isolated nucleic acid molecule which comprises the nucleotide sequence set forth in SEQ ID NO: 17. Also a part of the invention are those nucleic acid molecules which hybridize to a nucleic acid molecule containing the described nucleotide sequence, under stringent conditions. The term "stringent conditions" as used herein refers to parameters with which the art is familiar. More specifically, stringent conditions, as used herein, refers to hybridization in 3.5 x SSC, 1 x Denhardt's solution, 25 mM sodium phosphate buffer (pH 7.0), 0.5% SDS, and 2 mM EDTA for 18 hours at 65° C. This is followed by four washes of the filter, at 65° C. for 20 minutes, in 2 x SSC, 0.1% SDS, and one wash for up to 20 minutes in 0.3 x SSC, 0.1% SDS. There are other conditions, reagents, and so forth which can be used, which result in the same degree of stringency. The skilled artisan will be familiar with such conditions, and thus they are not provided herein.

It will also be seen from the examples that the invention includes the use of NAG encoding sequences in expression vectors, as well as in the transformation or transfection of host cells, cell lines and cell strains, including prokaryotic cells (e.g., *E. coli*), and eukaryotic cells (e.g., CHO or COS cells). The expression vectors require that the sequence be operably linked to a promoter. The expression vector may also include a nucleic acid sequence coding for HLA-A2. Where the vector contains both coding sequences, it can be used to transfect a cell which does not normally express either one. The tumor rejection antigen precursor coding sequence may be used alone, when, for example, the host cell already expresses HLA-A2. Of course, there is no limit on the particular host cell which can be used, as the vectors which contain the coding sequence may be used in HLA-A2 presenting cells if desired, and the nucleic acid molecule coding for NAG tumor rejection antigen precursor can be used in host cells which do not express HLA-A2.

The invention also includes expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the intron-expressed TRAPs of the invention, the invention shall be referred to as the NAG nucleic acid molecules and TRAPs. Also a part of the invention are the NAG antigenic peptides of SEQ ID NO: 6 and SEQ ID NO: 8. These NAG antigenic peptides can be used, for example, to identify those cells which present MHC molecule HLA-A2. Administration of the peptides, carrying a detectable signal, e.g., followed by the identification of cells to which the peptide has bound, is one way to accomplish this. Another way to accomplish this is the use of solid phase bound peptides, to which HLA-A2 presenting cells bind, thus removing them from the sample being assayed.

Additionally, the invention permits the artisan to diagnose a disorder characterized by expression of the NAG TRAP, particularly in the brain and in melanocytes. These methods involve determining expression of the NAG TRAP gene, and/or NAG TRAs derived therefrom, such as the NAG TRA presented by HLA-A2. In the former situation, such determinations can be carried out via any standard nucleic acid determination assay, including the polymerase chain reaction, or assaying with labelled hybridization probes. In the latter situation, assaying with binding partners for complexes of NAG TRA and HLA, such as antibodies, is especially preferred. An alternate method for determination is a TNF release assay, of the type described supra.

The isolation of the nucleic acid molecule encoding NAG TRAP also makes it possible to isolate the NAG TRAP molecule itself, especially NAG TRAP molecules containing the amino acid sequence coded for by SEQ ID NO: 17. These isolated molecules when presented as the NAG TRA, or as complexes of TRA and HLA, such as HLA-A2, may be combined with materials such as adjuvants to produce vaccines useful in treating disorders characterized by expression of the NAG TRAP molecule. In addition, vaccines can be prepared from cells which present the NAG TRA/HLA complexes on their surface, such as non-proliferative cancer cells and non-proliferative transfectants. In all cases where cells are used as a vaccine, these can be cells transfected with coding sequences for one or both of the components necessary to prove a CTL response, or can be cells which express both molecules without transfection. Further, the NAG TRAP molecule, its associated NAG TRAs, as well as complexes of NAG TRA and HLA, may be used to produce antibodies, using standard techniques well known to those skilled in the art.

When "disorder" is used herein, it refers to any pathological condition where the NAG tumor rejection antigen precursor is expressed. An example of such a disorder is melanoma in particular.

Therapeutic approaches based upon the disclosure are premised on a response by a subject's immune system, leading to lysis of NAG TRA presenting cells, such as HLA-A2. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein, are widely available, as are other suitable host cells.

To detail the therapeutic methodology, referred to as adoptive transfer (Greenberg, *J. Immunol.*, 136(5): 1917 (1986); Reddel et al., *Science*, 257: 238 (7–10–92); Lynch et al., *Eur. J. Immunol.*, 21: 1403–1410 (1991); Kast et al., *Cell*, 59: 603–614 (11–17–89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a NAG sequence. Once cells presenting the relevant complex are identified via the foregoing screening methodology, they can be combined with a sample from a patient, where the sample contains CTLs. If the complex presenting cells is lysed by the mixed CTL sample, then it can be assumed that a NAG derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., *Proc. Natl. Acad. Sci. USA*, 88: 110–114 (1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, for example, a Vaccinia virus or the bacteria BCG, and the materials de facto "infect" host cells. The cells which result present the complex of interest, and are recognized by autologous CTLs, which then proliferate. A similar effect can be achieved by combining the NAG tumor rejection antigen or the precursor itself with an adjuvant to facilitate incorporation into HLA-A2 presenting cells which present the HLA molecule of interest. The TRAP is processed to yield the peptide partner of the HLA molecule while the TRA is presented without the need for further processing.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. An isolated nucleic acid molecule consisting of the nucleotide sequence set forth in SEQ ID NO: 17.

2. An isolated nucleic acid molecule comprising a nucleotide sequence, the complimentary sequence of which hybridizes to the nucleotide sequence set forth in SEQ. ID. NO. 17 at 0.3 X SSC. 0.1% SDS.

3. An isolated molecule which is complementary to the nucleic acid molecule of claim 1, wherein said isolated molecule is mRNA or DNA.

4. A host cell transfected or transformed with the nucleic acid molecule of claim 1.

5. A host cell transfected or transformed with the nucleic acid molecule of claim 2.

6. An expression vector comprising the isolated nucleic acid molecule of claim 1 operably linked to a promoter.

7. An expression vector comprising the isolated nucleic acid molecule of claim 2 operably linked to a promoter.

8. The host cell of claim 4, wherein said host cell is a eukaryotic cell which expresses human leukocyte antigen-A2.

9. The host cell of claim 4, wherein said host cell is a prokaryotic cell which expresses human leukocyte antigen-A2.

10. The host cell of claim 5, wherein said host cell is a eukaryotic cell which expresses human leukocyte antigen-A2.

11. The host cell of claim 5, wherein said host cell is a prokaryotic cell which expresses human leukocyte antigen-A2.

12. The expression vector of claim 6, further comprising a nucleic acid molecule which codes for human leukocyte antigen-A2.

13. The expression vector of claim 7, further comprising a nucleic acid molecule which codes for human leukocyte antigen-A2.

14. An expression kit for purposes of expressing an intron-, expressed NAG tumor rejection antigen precursor comprising a separate portion of each of:

(i) the isolated nucleic acid molecule of claim 1, and (ii) a nucleic acid molecule which codes for human leukocyte antigen-A2.

15. An expression kit for purposes of expressing an intron-, expressed NAG tumor rejection antigen precursor comprising a separate portion of each of:

(i) the isolated nucleic acid molecule of claim 2, and (ii) a nucleic acid molecule which codes for human leukocyte antigen-A2.

16. The isolated nucleic acid molecule of claim 2, wherein said nucleic acid molecule codes for a tumor rejection antigen precursor (NAG).

* * * * *

UNITED STATES PATENT AND TRADEMARK OFFICE
CERTIFICATE OF CORRECTION

PATENT : 5,821,122

DATED : October 13, 1998

INVENTOR(S) : Guilloux et al.

It is certified that error appears in the above-identified patent and that said Letters Patent is hereby corrected as shown below:

On the title page, item [73] Assignee, should read as follows:

Lugwig Institute for Cancer Research
New York, NY

Signed and Sealed this

Twenty-ninth Day of February, 2000

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO. : 5,821,122
DATED : October 13, 1998
INVENTOR(S) : Guilloux et al.

It is certified that error appears in the above-identified patent and that said Letters Patent is hereby corrected as shown below:

In cover page, line [21] change "487,135" to - - 08/487,135 - -.
In column 2, line 48, change "X" to - - λ - -.
In column 7, line 57, change "CDNA" to - - cDNA - -.
In column 7, line 57, change "CDNA" to - - cDNA - -.
In column 9, line 10, change "CDNA" to - - cDNA - -.
In column 9, line 14, change "CDNA" to - - cDNA - -.
In column 10, line 1, change "DNTP" to - - dNTP - -.
In column 10, line 41, change "samples" to - - sample - -.
In column 11, line 35, change "tumor" to - - tumors - -.
In column 24, line 44, change "intron-,expressed" to - - intron-expressed - -.

Signed and Sealed this

Twenty-third Day of May, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO. : 5,821,122
DATED : October 13, 1998
INVENTOR(S) : Guilloux, et. al.

It is certified that error appears in the above-identified patent and that said Letters Patent is hereby corrected as shown below:

On the <u>cover page</u>, <u>item [73]</u>, under the heading Assignee, add after the word France "Ludwig Institute for Cancer Research" to read as -- INSERM (Institute Nat'l de la Sante et de la Recherche . .), Paris, France
Ludwig Institute for Cancer Research, New York, NY --.

Signed and Sealed this

Twenty-fourth Day of October, 2000

Attest:

Q. TODD DICKINSON

*Attesting Officer*      *Director of Patents and Trademarks*